US00PP10389P

United States Patent [19]

Sorensen

[11] Patent Number: Plant 10,389

[45] Date of Patent: May 12, 1998

[54] OSTEOSPERMUM PLANT NAMED 'CAPE DAISY ZULU'

[75] Inventor: Carl Aksel Kragh Sorensen, Åbyhoj, Denmark

[73] Assignee: Paul Ecke Ranch, Encinitas, Calif.

[21] Appl. No.: 695,306

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 9,897 5/1997 Perry ..... Plt./68.1

*Primary Examiner*—Howard J. Locker
*Assistant Examiner*—Kent L. Bell
*Attorney, Agent, or Firm*—Arnold, White & Durkee

[57] ABSTRACT

A new and distinct cultivar of Osteospermum named 'Cape Daisy Zulu', particularly characterized by its upright growth habit with excellent bright yellow flower color, mid-season flowering and medium green foliage, and suitability to 6 inch pots and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Zulu', and was developed by the inventor Carl Aksel Kragh Sorensen in Aarhus, Denmark by crossing Osteospermum 'Buttermilk' and an unnamed cultiver of *Dimorphotheca chrysanthemifolia.*

Asexual reproduction by terminal (stem tip) cuttings taken by me or under my supervision in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique dark yellow flower color.
2. An upright growth habit.
3. Unique foliage shape.
4. Well suited for 6" pots, nursery containers, and hanging baskets. 'Cape Daisy Zulu' is similar to the unpatented cultivar 'Wild Yellow'. The growth habit of 'Cape Daisy Zulu' is more compact, it flowers earlier, and has a smaller flower diameter than 'Wild Yellow'.

DESCRIPTION OF PHOTO

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, California. Three rooted cuttings were transplanted into 26 cm (10 inch) hanging baskets on Sep. 25, 1995. Plants were pinched on Oct. 16, 1995, and received plant growth regulator on Nov. 6, 1995. The values, measurements and observations noted below were taken from plants in bloom on Mar. 4, 1996.

On Apr. 21, 1996, I observed a plant in a 32.5 cm nursery pot 23 cm tall. This nursery pot had three branched plants with an overall height of 71 cm and an overall width of 86 cm. Each plant had 4 strong branches, originating at the soil line, for a total of 12 branches. Each branch was approximately 43 cm long terminating in a flower. At observation of the three plants, there were 80 flowers open and 136 flower buds in various stages of development. Approximately 6 shoots subtend the terminal flower from the top 6 nodes on the primary shoot. These secondary shoots also terminated in a flower.

Color references are made to The Royal Horticultural Society Colour Chart (RHS), except where general terms of ordinary dictionary significance are used.

THE PLANT

Origin: Seedling from cross pollination.

Parentage: Cross between Seed Parent Osteospermum 'Buttermilk' and Pollen Parent an unnamed *Dimorphotheca chrysanthemifolia* cultivar.

Classification:

*Botanical.*—*Osteospermum ecklonis.*

*Common name.*—Osteospermum.

*Cultivar name.*—'Cape Daisy Zulu'.

Asexual reproduction:

A. *Cutting type.*—Vegetative shoot tip with stems approximately 3 cm long and developing to 4-5 cm after 28 days in propagation.

B. *Time to initiate roots.*—14 days at 20° C.; nicely developed root mass in 28 days.

C. *Rooting habit.*—Numerous, fibrous adventitious roots from the stem base.

Plant description:

A. *Form.*—Symmetrical, upright growing perennial shrub, with good branching characteristics after pinching, giving the plant a full appearance.

B. *Habit of growth.*—Vigorous, mounding habit, producing approximately 26 leaves per stem and terminating in flowers. Growth is determinate and flowering on secondary shoots is continuous in cool climates.

C. *Foliage description.*—1. Leaf shape: Obovate and dentate with three major lobes on either side of the leaf blade with acute tip and attenuate leaf base. 2. Leaf blade size: Mature leaves 7 cm long and 3.5 cm wide. 3. Petiole length: Approximately 2 cm in length. 4. Leaf Margin: Slightly sinuate with 3-5 additional small, pointed lobes on either side of the lobed leaf blade. 5. Leaf texture: Slightly undulant and twisted at the tip. i) Upper surface: Slightly pubescent with short, white trichomes evenly distributed throughout the leaf surface. ii) Under surface: Glabrous. 6. Leaf color: Dark green. i) Upper surface: Near RHS 147A. ii) Under surface: Between RHS 147 A-B. 7. Venation: Palmately branched with one predominate light green colored mid-vein on upper surface. The mid-vein is raised on the lower surface. 8. Fragrance: Fragrance is that characteristic of Osteospermum plant species, particularly noted when foliage is wet.

Inflorescence description: Daisy type composite flower with disc florets and ray florets that close at night and open in the morning. One ray floret subtends each pistillate flower part. The disc florets contain male flower parts.

A. *Flowering habits.*—Flowering is determinate with one primary flower at the end of a long (15-20 cm) pedicel on open flowers. Each pedicel had approximately 7 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates.

C. *Flower buds.*—Flower buds develop successively on secondary branches, reaching a size of 2.5 cm long and 1.4 cm wide prior to opening.

D. *Flowers borne.*—Singularly 10 cm above the plant canopy.

E. *Quantity of flowers.*—Secondary flowers occur progressively around the primary flower so that tight buds to mature flowers are visible at the same time.

F. *Florets.*—1. Number of florets: 29-37 ray florets and numerous disc florets, making up a flower disk approximately 2.1 cm in diameter. 2. Shape: Narrow linear florets with obtuse to acute tips and acute bases. Rayflorets are approximately 4.2 cm long and 1 cm wide. 3. Color: Ray florets are bright yellow; disc florets are yellow. i) Upper surface of ray florets: Near RHS 9B. ii) Under surface of ray florets: Peripherally-yellow, near RHS 9A; broad stripe down midrib, grey/orange, near RHS 175D. iii) Disc florets: Near RHS 7A. 4. Surface: i) Upper surface of ray florets: Glabrous. ii) Under surface of ray florets: Glabrous but pubescent near the base. 5. Inflorescence Up to 8.5 cm in diameter. 6. Fragrance: None.

G. *Reproductive organs.*—1. Stamens: Short stamens emerge on outermost disc florets and progress toward the center. 2. Anther: Each disc florets has 1 stamen terminating in a 5-part anther. 3. Pollen: Copious and golden yellow. 4. Stigma: Bipartite 5. Styles: Short, approximately 3 mm long and yellow. 6. Ovary: Inferior to both disc and ray florets and green in color. 7. Ray Florets contain pistillate flower parts, Disc florets contain staminate flower parts.

What is claimed is:

1. A new and distinct cultivar of Osteospermum plant named 'Cape Daisy Zulu', as illustrated and described.

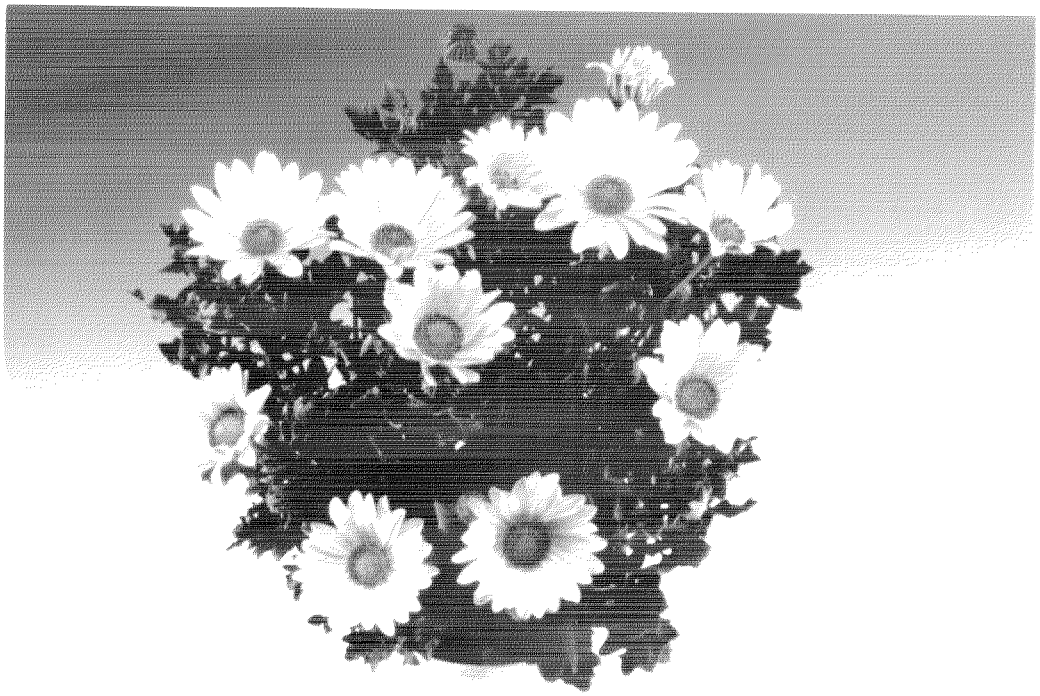

* * * * *